United States Patent
St. Laurent et al.

(10) Patent No.: US 9,987,246 B2
(45) Date of Patent: Jun. 5, 2018

(54) 4-BENZYLSULFONYL-2-BUTENENITRILE

(71) Applicant: Olatec Therapeutics LLC, New York, NY (US)

(72) Inventors: Joseph P. St. Laurent, Lakeville, MA (US); Gerald S. Jones, Norwood, MA (US); David M. Bresse, Middlleboro, MA (US); Scott A. Goodrich, Stoughton, MA (US)

(73) Assignee: Olatec Therapeutics LLC, New York, NY (US)

( * ) Notice: Subject to any disclaimer, the term of this patent is extended or adjusted under 35 U.S.C. 154(b) by 0 days. days.

(21) Appl. No.: 15/245,513

(22) Filed: Aug. 24, 2016

(65) Prior Publication Data

US 2016/0361286 A1    Dec. 15, 2016

Related U.S. Application Data

(63) Continuation of application No. PCT/US2015/017049, filed on Feb. 23, 2015.

(60) Provisional application No. 61/944,527, filed on Feb. 25, 2014.

(51) Int. Cl.
*A61K 31/277* (2006.01)
*C07C 317/28* (2006.01)
*A61K 31/10* (2006.01)
*A61K 9/00* (2006.01)

(52) U.S. Cl.
CPC .......... *A61K 31/277* (2013.01); *A61K 9/0014* (2013.01); *A61K 9/0019* (2013.01); *A61K 9/0053* (2013.01); *A61K 31/10* (2013.01); *C07C 317/28* (2013.01)

(58) Field of Classification Search
None
See application file for complete search history.

(56) References Cited

U.S. PATENT DOCUMENTS

| | | | |
|---|---|---|---|
| 7,989,495 B2 | 8/2011 | Kuwada et al. | |
| 9,440,916 B2 * | 9/2016 | St. Laurent | C07C 317/44 |
| 9,481,644 B2 * | 11/2016 | St. Laurent | A61K 47/10 |
| 9,522,878 B2 * | 12/2016 | St. Laurent | C07C 317/28 |
| 2011/0250509 A1 | 10/2011 | Yamaguchi et al. | |
| 2013/0324601 A1 * | 12/2013 | St. Laurent | A61K 31/277 |
| | | | 514/520 |
| 2015/0087701 A1 | 3/2015 | St. Laurent et al. | |
| 2015/0182488 A1 | 7/2015 | St. Laurent et al. | |
| 2016/0206589 A1 | 7/2016 | St. Laurent et al. | |

FOREIGN PATENT DOCUMENTS

| | | |
|---|---|---|
| WO | 2013/184586 A1 | 12/2013 |
| WO | 2013/184708 A1 | 12/2013 |
| WO | 2014/043144 A1 | 3/2014 |

OTHER PUBLICATIONS

Pubchem, "Compound Summary for CID 64691799", Created Date: Oct. 23, 2012. [ retrieved on Apr. 22, 2015]. Retrieved from the Internet. <URL: ttps://pubchem.ncbi.nlm.nih.gov/summary/summary.cgi?from=compound&cid=64691799> entire document.
Tanii, et al., "Repeated Exposure to Cruciferous Allyl Nitrile Protects against Chemically Induced Skin Inflammation in the Mouse", Food and Nutrition Sciences, 3 (8): pp. 1037-1042, 2012 entire document.
Supplementary European Search Report dated Sep. 25, 2017 of EP Application No. 15754442.0 (2 pages).

* cited by examiner

*Primary Examiner* — Leslie A. Royds Draper
(74) *Attorney, Agent, or Firm* — Perkins Coie LLP; Viola T. Kung

(57) ABSTRACT

The present invention is directed to a pharmaceutical composition comprising a pharmaceutically acceptable carrier and 4-benzylsulfonyl-2-butenenitrile, or a pharmaceutically acceptable salt or solvate thereof. The present invention is directed to a method for treating inflammation, inflammatory-related disorders, or pain, by administering 4-benzylsulfonyl-2-butenenitrile, or a pharmaceutically acceptable salt or solvate thereof to a subject in need thereof.

14 Claims, 1 Drawing Sheet

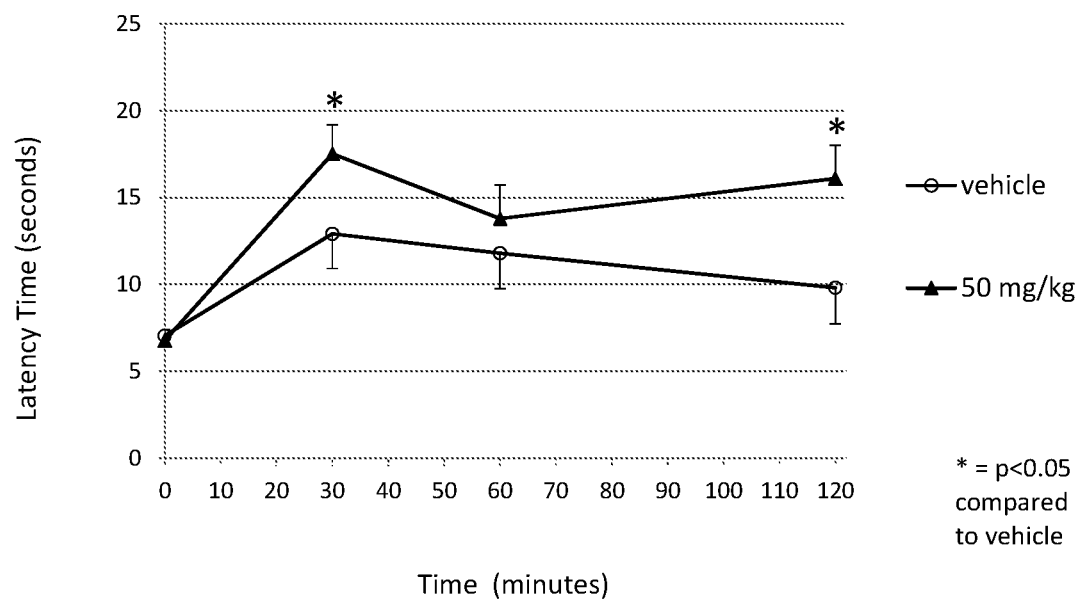

4-BENZYLSULFONYL-2-BUTENENITRILE

This application is a Continuation of PCT/US2015/017049, filed on Feb. 23, 2015; which claims priority to U.S. Provisional Application No. 61/944,527, filed Feb. 25, 2014; the contents of the above identified applications are incorporated herein by reference in their entirety.

FIELD OF THE INVENTION

The present invention relates to 4-benzylsulfonyl-2-butenenitrile, or its pharmaceutically acceptable salts or solvates thereof. The present invention also relates to a pharmaceutical composition comprising the compound and a pharmaceutically acceptable carrier.

BRIEF DESCRIPTION OF THE DRAWINGS

FIG. 1 shows the results of tail flick test of mice treated with vehicle (DMSO), test compound (50 mg/kg in vehicle) by intraperitoneal application. The latency time of each group is calculated as mean±SEM and plotted against time, where * indicates p value <0.05 compared with vehicle-treated mice.

DETAILED DESCRIPTION OF THE INVENTION

Definitions

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

"Solvates," as used herein, are addition complexes in which the compound is combined with an acceptable co-solvent in some fixed proportion. Co-solvents include, but are not limited to, ethyl acetate, myristyl lactate, cetyl lactate, isopropyl myristate, ethanol, 1-propanol, isopropanol, 1-butanol, isobutanol, tert-butanol, acetone, methyl ethyl ketone, and diethyl ether.

4-Benzylsulfonyl-2-butenenitrile

The inventors have synthesized and identified 4-benzylsulfonyl-2-butenenitrile. The compound or its pharmaceutically acceptable salt or solvate is effective for treating inflammation, inflammatory-related disorders, and pain.

4-Benzylsulfonyl-2-butenenitrile has a formula weight of 221.28, and its trans and cis structures are shown below.

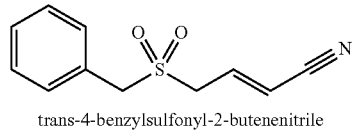

trans-4-benzylsulfonyl-2-butenenitrile

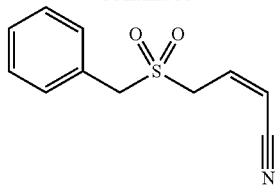

cis-4-benzylsulfonyl-2-butenenitrile

4-Benzylsulfonyl-2-butenenitrile can be synthesized by heating an aqueous solution of sodium benzylsulfinate with 4-bromo-2-butenenitrile under pressure. The requisite 4-bromo-2-butenenitrile can be prepared by bromination of allyl cyanide, followed by base-catalyzed elimination of HBr, which result in an approximately 1:1 mixture of E- and Z-isomers.

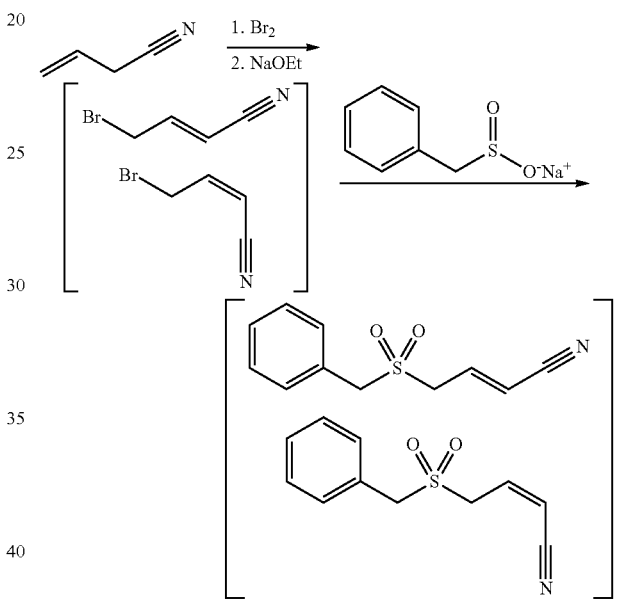

Pharmaceutical Compositions

The present invention provides pharmaceutical compositions comprising one or more pharmaceutically acceptable carriers and an active compound of 4-benzylsulfonyl-2-butenenitrile, or a pharmaceutically acceptable salt or a solvate thereof. The pharmaceutical composition can include one of the cis or trans isomers, or both isomers either equimolar, or of different amounts. The active compound or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in a dosage form such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Other pharmaceutically acceptable carriers include xanthan gum, carrageenan, Avicel RC-591 (a combination of microcrystalline cellulose and), and polyethylene glycol. Alternately, the active compound may be dissolved or suspended in a pharmaceutically acceptable lipid formulation such as those described by Kalepu et al (Acta Pharmaceutica Sinica B, 3: 361-372, 2013), for example, vegetable oil, coconut oil, castor oil, etc.

Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, diethylene glycol monoethyl ether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid is a component of membrane phospholipids. After it is freed from phospholipids, arachidonic acid acts as a precursor to many of the known eicosanoids including prostaglandins and leucotrienes, which are known pro-inflammatory entities.

The active compound is effective in inhibiting pro-inflammatory cytokine release (e.g., IL-1β, IL-6, TNFα, IL-4 and IFNγ) from human peripheral blood mononuclear cells in vitro. The active compound is anti-inflammatory when applied topically in the mouse ear swelling model, in which the inflammation is induced by arachidonic acid.

The present invention is directed to a method of treating inflammation and/or pain. 4-benzylsulfonyl-2-butenenitrile, can be used as is, or it can be administered in the form of a pharmaceutical composition that additionally contains a pharmaceutically acceptable carrier. The method comprises the steps of first identifying a subject suffering from inflammation and/or pain, and administering to the subject the active compound, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestations of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes nociceptive, neuropathic, and mix-type. The present invention reduces pain of varying severity, i.e. mild, moderate and severe pain; acute and chronic pain. The present invention is effective in treating joint pain, muscle pain, tendon pain, burn pain, and pain caused by inflammation such as rheumatoid arthritis.

In one embodiment, the present invention is useful in treating inflammation and/or pain associated in a musculoskeletal system. The highly innervated, musculoskeletal system has a high capacity for demonstration of pain. In addition, the musculoskeletal system has a high capacity for tissue swelling. In musculoskeletal system, the degree of tissue damage is frequently magnified out of proportion to the resulting inflammatory response.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. "The active compound," as used herein, is intended to include the compound (cis-isomer, trans-isomer, or a mixture thereof) and its pharmaceutically acceptable salts or solvate thereof. The skeletal or muscular diseases or conditions include musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

In one embodiment, the present invention is directed to a method of treating inflammation and/or pain associated with gout. Gout is a chronic inflammatory disease that is characterized by recurrent, sudden, and severe attacks of acute inflammation (redness and tenderness) and pain at the joints, often at the base of the big toe. Gout is caused by elevated levels of uric acid in the blood. Gout is a type of arthritis. Some people may develop chronic gout, which is also called gouty arthritis.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of the active compound delivered can vary; but are generally $1 \times 10^{-10}$-$1 \times 10^{-4}$ moles/liter, and preferably $1 \times 10^{-8}$-$1 \times 10^{-5}$ moles/liter.

In one embodiment, the composition is applied topically onto the affected area and rubbed into it. The composition is topically applied at least 1 or 2 times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally at least 0.1 mg/kg/day and less than 100 mg/kg/day. For example, the dosage for oral administration is 0.1-100 or 0.5-50 mg/kg/day, and preferably 1-20 or 1-10 mg/kg/day for a human subject. For example, the dosage for oral administration is 20-1000 mg/day, and preferably 20-500, 20-100, 25-200, 50-500, 50-200, 100-600, 100-400, or 200-800 kg/day in a human subject.

In one embodiment, the pharmaceutical composition is administrated intravenously to the subject. The dosage for intravenous bolus injection or intravenous infusion is generally 0.03 to 20 and preferably 0.03 to 10 mg/kg/day.

In one embodiment, the pharmaceutical composition is administrated subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1. Preparation of 4-benzylsulfonyl-2-butenenitrile

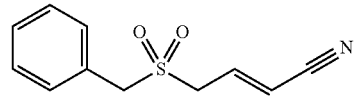

4-benzylsulfonyl-2-butenenitrile ($C_{11}H_{11}NO_2S$; FW 221.28)

(A) A solution of allyl cyanide (0.59 mole) in t-amyl alcohol (120 mL) and petroleum ether (370 mL) was treated sequentially with a solution of bromine (0.59 mole) in t-amyl alcohol (60 mL), followed by an ethanolic solution of sodium ethoxide (345 mL, 0.60 mole). When the reaction mixture had cooled to room temperature, solids were removed by vacuum filtration and the filtrate was concentrated under reduced pressure. The residual liquid was charged on a silica gel column (307.10 g) and eluted with hexanes-ethyl acetate (19:1; 9:1). Combination of appropriate fractions, followed by concentration under reduced pressure gave 4-bromo-2-butenenitrile as a pale yellow liquid (47.14 g).

(B) Benzylsulfonyl chloride (10.5 mmol) in one portion was added to a stirred solution of sodium sulfite (10.5 mmol) and sodium bicarbonate (20.9 mmol) in water (20 mL) in a 50 mL pressure vessel at room temperature. After a few minutes, the vessel was placed in an oil bath at 50° C., and stirring was continued for 2 hours, after which the vessel was removed from the bath, tightly sealed and stored at room temperature overnight.

(C) The product from part (A) (20.4 mmol) was added to the vessel containing the aqueous solution prepared in part (B). The vessel was tightly sealed, placed in an oil bath at 110° C., and heating/stirring was continued for 12 hours. After the vessel had stood at room temperature overnight, a brown solid was collected by vacuum filtration, and washed with water. After air-drying, the solid was taken up in acetone (50 mL), and treated with activated charcoal (1 g). The mixture was vacuum filtered through a Whatman GF/F glass fiber filter, and the filtrate was concentrated under reduced pressure to a lighter brown solid, which was dissolved in a mixture of acetic acid (20 mL) and water (48 mL) at ~80° C. with stirring. The flask containing the solution was sealed and stored at room temperature overnight. A beige-colored crystalline solid was collected by vacuum filtration, and washed with cold aqueous acetic acid, and allowed to air-dry.

Yield: 1.367 g (72% recovery; 59% isolated yield based on benzylsulfonyl chloride). mp: 89.4-91.4° C.; FTIR: 2226 cm$^{-1}$ (CN); Calculated for $C_{11}H_{11}NO_2S$: C, 59.71; H, 5.01; N, 6.33. Found: C, 59.64; H, 4.87; N, 6.35.

Example 2. NMR Spectrum

The $^1H$ NMR spectrum for 4-benzylsulfonyl-2-butenenitrile was acquired in $CDCl_3$ solution at 400 MHz by Spectral Data Services, Inc. (SDS). The chemical shift data are shown in Table 1.

TABLE 1

$^1H$ Chemical shifts (ppm) for 4-benzylsulfonyl-2-butenenitrile.

| Chemical Shift (ppm) | RIV$^a$ | Number of Protons | Multiplicity | Assignment |
|---|---|---|---|---|
| >3 | 0.83 | | | impurities (9 signals) |
| 3.25 | 0.02 | | | impurity |
| 3.70 | 11.37 | 1 | dd | $SO_2C\underline{H}_2CH\!=\!CHCN$ (1) |
| 3.97 | 9.59 | 1 | dd | $SO_2C\underline{H}_2CH\!=\!CHCN$ (1) |
| 4.29 | 21.16 | 2 | d | $C_6H_5C\underline{H}_2$ |
| 5.5-5.6 | ~5 | ½ | dt (J~16 Hz) | $SO_2CH_2CH\!=\!C\underline{H}CN$ (E) |
| 5.6-5.7 | ~5 | ½ | dt (J~11 Hz) | $SO_2CH_2CH\!=\!C\underline{H}CN$ (Z) |
| 6.45-6.6 | 10.12 | 1 | m | $SO_2CH_2C\underline{H}\!=\!CHCN$ (E,Z) |
| 7.3-7.5 | 51.46 | 5 | m | $C_6H_5$ |

$^a$Relative Integration Value

The structure of 4-benzylsulfonyl-2-butenenitrile comprises 11 protons. All protons are accounted for and occur at reasonable chemical shifts. Chemical shift assignments for the benzyl protons are unequivocal, as are those for the remaining methylene protons. The two pairs of triplets at 5.5-5.6 ppm and 5.6-5.7 ppm can be distinguished by their coupling constants (J). J~16 Hz is consistent with the coupling constant expected for alkene protons in an E-configuration, whereas J~11 Hz is consistent with the coupling constant expected for alkene protons in a Z-configuration. Based on a comparison of RIV values for these signals, the E/Z ratio is nearly 1, with a slight preference for the E-isomer. Coupling constants for the remaining alkene protons cannot be measured exactly due to the complexity of the signal at 6.45-6.6 ppm.

TLC (chloroform/ethanol (19:1), detected at 254 nm and with potassium permanganate reagent) shows two discrete and partially overlapping spots, corroborating the NMR result that the product of Example 1 is a mixture of E- and Z-isomers of about 1 to 1 ratio.

Example 3. Gel Formulation

Table 2 illustrate a gel formulation.

TABLE 2

|  | 5% Gel | 1% Gel |
|---|---|---|
| Active compound | 5.0% | 1.0% |
| Dow Corning Elastomer Blend EL-8050 ID | 61.4% | 63.4% |
| Labrafac Lipophile WL 1349 | 8.6% | 8.6% |
| Octisalate | 5.0% | 5.0% |
| Lauryl Lactate | 1.0% | 3.0% |
| Methyl Laurate | 5.0% | 7.0% |
| Dow Corning 556 Cosmetic Grade Fluid | 5.0% | 7.0% |
| Squalene | 2.0% | 2.0% |
| Sunflower Seed Oil | 2.0% | 2.0% |
| Diethylene Glycol Monoethyl Ether | 5.0% | 3.0% |
| Total | 100.0% | 100.0% |

Example 4. Analgesic Activity of Active Compound by Intraperitoneal Administration in Mice (Tail Flick Model)

Tail flick test is a test of the pain response in animals. Tail flick test is used in basic pain research and to measure the effectiveness of analgesics, by observing the tail flick reaction to heat in an animal. This test assesses the nociceptive response to a local pain stimulus, and the ability of a drug to inhibit this response.

Vehicle control (dimethyl sulfoxide, DMSO) and test compound 4-benzylsulfonyl-2-butenenitrile in DMSO were administered intraperitoneally to mice with a volume of 5 mL/kg, twice, at 30 minutes before the first tail flick measurement. The test compound was administered at a dosage of 50 mg/kg. The positive control compound morphine was administered by subcutaneous injection at 8 mg/kg with a volume of 8 mL/kg, at 30 minutes before the first tail flick measurement. Each group had 10 mice.

The response of mice to heat stimulus was evaluated by measuring the time of tail-flick or tail-flick latency from 49° C. water bath. Briefly, the animal was placed in a restrainer with its tail hanging down. Approximately 2 inches of the tail was immersed in a beaker of water at 38±1° C. for about 30 seconds, and this was done twice to acclimate the animal to the procedure.

Subsequently, approximately 2 inches of the tail was immersed in a beaker of water at 49±1° C., at which point a timer was started. At the first sign of discomfort (whole body jerk, curvature or rapid movement of the tail), or at 30 seconds if the animal did not response, the timer was stopped, the latency time was recorded, and the tail was removed from the water.

Tail flick measurements were made 30, 60 and 120 minutes post administration of the dosage of test compound. An ANOVA was done, and if $p<0.05$, a Dunnett's t test was employed to calculate significant difference between vehicle control and test compound treated groups. A pairwise Student's t test was used to calculate differences between the morphine group and the control group.

FIG. 1 shows the results of tail flick of mice treated with vehicle (DMSO) and test compound (50 mg/kg in DMSO) The latency time of each group is calculated as mean±SEM (standard error of mean) and plotted against time, where * indicates p value <0.05 compared with vehicle-treated mice.

As shown in FIG. 1, the vehicle (DMSO) at 5 mL/kg shows some analgesic effects when compared with time zero. Mice treated with test compound by intraperitoneal administration at 50 mg/kg show statistically significant tail flick latency at 30 minutes (p value=0.046) and 120 minutes (p value=0.020), when compared with vehicle-treated mice. Morphine-treated mice (subcutaneous injection) show statistically significant tail flick latency at 30 and 60 minutes, but not at 120 minutes, when compared with vehicle-treated mice. Morphine's data are not included in FIG. 1.

The above results provide evidence that test compound when administered intraperitoneally, is effective in treating nociceptive pain in an animal. Intraperitoneal administration in mice is a good representation of the pharmacokinetic profile from other parenteral routes of administration (e.g., intravenous, subcutaneous, intramuscular). Therefore, the results indicate that parenteral administration of the test compound to a subject may be effective in reducing nociceptive pain.

Example 5. Analgesic Activity of Active Compound by Oral Administration in Mice, Formalin Model (Prophetic Example)

Formalin test is a model of continuous pain resulting from formalin-induced tissue injury. Nociceptive and inflammatory pain was induced by injection of a dilute formalin solution into the paw, resulting in nocifensive behavior including paw flinching. The formalin model encompasses inflammatory, neurogenic, and central mechanism of pain. The early phase of pain (from 0 to about 10 minutes) is due to nociceptive mechanism and the late phase of pain (from 10-40 minutes) is due to a combination of inflammatory pain and nociceptive mechanism. Pain behavior is assessed using manual paw licking measurements. The endpoints of the study are the number of paw licking events. (Hunskaar et al., *Pain*, 30:103-114, 1987; Li et al., *Molecular Pain*, 6:11, 2010)

Male CD-1 mice are used in the study.

Immediately prior to testing (at time 0), mice are restrained in a cloth and injected with 20 μL of a 5% formalin solution, subcutaneously into the dorsal surface of the left hind paw. Vehicle control (n=10, DMSO) and test 4-benzylsulfonyl-2-butenenitrile (n=10, in DMSO) are administered by oral gavage with a volume of 10 mL/kg to mice. The amounts of test compound are 50 or 100 mg/kg per dose.

Positive control morphine is administered by subcutaneous injection at 4 mg/kg with a volume of 4 mL/kg to mice (n=10).

Morphine is subcutaneously administered once 15 minutes before formalin injection. The test compounds and vehicle control are orally administered twice (BID), at 60 and 15 minutes before formalin injection at time zero.

Following formalin injection, animals are placed in individual cages, and manually observed for 60 minutes. The licking events are recorded in five minute intervals continuously for a total of 60 minutes. The number of licking events per minute is calculated between 0-10 minutes and 10-40 minutes for vehicle, positive control, and test compound. A two-sample t-test was done to compare the vehicle group with the test compound group. Significance is set at P<0.05 level.

Example 6. Analgesic Activity of Active Compound by Topical Administration in Mice, Formalin Model (Prophetic Example)

The animals and the treatment protocol are similar to those described in Example 5, except the following.

The test compound 4-benzylsulfonyl-2-butenenitrile (375 mM in vehicle, n=10) and vehicle control (acetone:ethanol 1:1, n=10) are administered topically by submerging the mouse left hind paw in the respective solution for about 30 seconds. The paw is then withdrawn and wiped with tissue to avoid excess dermal drying.

Positive control morphine is administered by subcutaneous injection at 4 mg/kg with a volume of 4 mL/kg to mice (n=10).

Morphine is subcutaneously administered once 15 minutes before formalin injection. The test compounds and vehicle control are topically administered twice (BID), at 90 and 15 minutes before formalin injection.

Example 7. Anti-Inflammatory Activity of Active Compound by Topical Application in Mice in an Arachidonic Acid Model (Prophetic Example)

4-Benzylsulfonyl-2-butenenitrile is used in this experiment.

The test compound, indomethacin (positive control), and vehicle (acetone:ethanol/1:1) are evaluated for anti-inflammatory activity in a topical arachidonic acid-induced ear swelling model in mice.

Male ICR mice are used and randomly divided. Arachidonic Acid (0.5 mg in 20 μl of acetone:ethanol/1:1) is applied topically to the anterior and posterior surfaces of the right ear of each mouse. Test substances (375 mM in vehicle) and vehicle are similarly applied 30 min before and 15 min after arachidonic acid application. The thickness of the right ear and the left ear are measured and the difference calculated as an indication of the inflammation in the right ear. Ear swelling is measured by a Dyer model micrometer gauge at 60 and 90 minutes after arachidonic acid application as an index of inflammation. Percent inhibition is calculated according to the formula: Ic−It/Ic×100, where Ic and It refers to increase of ear thickness (mm) in control and treated mice, respectively. ANOVA and Dunnett's test are employed to ascertain significant difference between vehicle control and treated groups. Significance is set at P<0.05 level.

Example 8. Anti-Inflammatory Activity of Active Compound in Mice by Oral Application in an Arachidonic Acid Model (Prophetic Example)

The protocols are similar to those described in Example 7 except the following.

The active compound 4-benzylsulfonyl-2-butenenitrile is suspended in a vehicle (1% Tween 80 in water suspension or a lipid-based pharmaceutically acceptable carrier) to 5-15 mg/mL. The test compound, dexamethasone (positive control in vehicle), and vehicle are orally administered to mice and evaluated for anti-inflammatory activity in the topical arachidonic acid induced ear swelling model in mice.

Test compound in vehicle (50 mg/kg, 10 mL/kg) and vehicle (10 mL/kg,) are orally administered by gavage 1 hour before arachidonic acid, whereas dexamethasone is orally administered by gavage 3 hour before arachidonic acid challenge.

Example 9. Anti-Inflammatory and Analgesic Activity of Active Compound in a Carrageenan Model by Topical Application (Prophetic Example)

Test materials in vehicle, indomethacin (positive control), and vehicle (acetone:ethanol 1:1), are evaluated for anti-inflammatory and analgesic activity in the rat carrageenan-induced paw inflammation model.

Rats are used in the experiment. Carrageenan (0.1 mL of a 1% suspension) is injected subcutaneously into the left hind paw to induce inflammation. Test material (1-5%) or vehicle is applied to the paw topically at volumes of 0.05, 0.1 0.15 or 2.0 mL, 1.5, 2.5, and 3.5 hours following the carrageenan administration. Indomethacin is given orally at 5 mg/kg, 1 hour prior to carrageenan administration. The degree of inflammation (edema, or swelling) is determined using a plethysmograph to measure paw volume. Analgesia is determined by measuring paw withdrawal to a mechanical stimulus using von Frey filaments. Inflammation and analgesia are measured 4 hours after carrageenan administration. Test materials are expected to have anti-inflammatory and/or analgesic properties as measured by a significant decrease in paw volume and/or a significant increase in mechanical pressure needed to elicit paw withdrawal, respectively, as compared to the vehicle control.

Example 10. Analgesic Activity of Active Compound in CFA-Induced Thermal Hyperalgesia (Prophetic Example)

CFA (Complete Freund's Adjuvant) is known to induce inflammatory pain. (Walker, et al. JPET. 304: 56-62, 2003.)

Male Sprague-Dawley rats weighing 180±20 g are used. The animals, divided into groups of 8-10 each, receive a subplantar injection (0.1 ml) of CFA (0.1% solution) to the tested hind paw at 24 hours prior to experimentation. Thermal hyperalgesia is tested by using the IITC Model-336G (IITC INC. USA) apparatus with a thermally regulated glass floors set at 30° C. Each rat is placed within a plastic box atop a glass floor. A light beam under the floor is aimed at the plantar surface of the right hind paw. The time is measured automatically when the paw is withdrawn away from the thermal stimulus. The intensity of the light is adjusted with average group baseline latency from 12 to 14 sec (pre-CFA) and a cut-off latency of 20 sec imposed. The latency to withdrawal is obtained for each rat and defined as the heat pain threshold. Twenty four hours after CFA injection, rats are pre-selected (with clear presence of thermal hyperalgesia) for experimentation only if the latency to withdrawal is less than 75% of baseline.

The active compound 4-benzylsulfonyl-2-butenenitrile is prepared in a topical vehicle or in an oral vehicle.

Active compound in topical or oral vehicle, morphine (positive control, p.o., 20 mg/kg), topical vehicle (acetone: ethanol 1:1), and oral vehicle (DMSO) are evaluated for analgesic activity in the formalin model.

Test substance or vehicle is either administered orally (20-60 mg/kg) or topically (375 mM) to the plantar surface of the hind paw, at 60 minutes before the level of thermal hyperalgesia is again measured (post-treatment). Mean±SEM of thermal paw withdrawal time is calculated. Unpaired Student's t test is applied for comparison the values of post-treatment between test substance treated group and vehicle control group. Positive activity is considered at $P<0.05$.

Example 11. Analgesic Activity of Active Compound in Chronic Constriction Injury Model (Prophetic Example)

Peripheral nerve lesions may generate a syndrome comprising, in addition to spontaneous pain, exaggerated responses to light touch (tactile allodynia). Chronic constriction injury model is a neuropathic pain model.

Male Sprague Dawley rats weighing 180±20 g are used. Under pentobarbital (50 mg/kg, 5 ml/kg, i.p.) anesthesia, the sciatic nerve is exposed at mid-thigh level. Four ligatures (4-0 chromic gut), about 1 mm apart, are loosely tied around the nerve. The animals are then housed individually in cages with soft bedding for 7 days before testing. Constriction of the sciatic nerve produces nerve injury and unilateral neuropathic pain.

On the day of experiments, the animals have no access to food overnight before testing. The rats are placed under inverted plexiglass cages on a wire mesh rack and allowed to acclimate for 20 to 30 minutes. Mechanic allodynia is evaluated by the Chaplan up/down method using von Frey filaments to the plantar surface of the left hind paw. See Chaplan, et al. J. Neuroscience Methods, 53: 55-63, 1994.

Rats are pre-selected for experimentation only if the pain threshold 7-14 days after nerve ligation (pre-treatment) is reduced by 10 grams of force relative to the response of the individual paw before nerve ligation (pre-ligation), namely, with clear presence of allodynia.

Active compound in topical or oral vehicle, morphine (positive control, p.o., 20 mg/kg), topical vehicle (acetone: ethanol 1:1), and oral vehicle (DMSO) are evaluated for analgesic activity in the formalin model.

Test substance or vehicle is either administered orally (20-60 mg/kg) or topically (375 mM) to the plantar surface of the left hind paw. The mechanical allodynia test is performed 30 min before (pre-treatment) and 1 and 3 hours after a single dose of test substance or vehicle (post treatment). Paw withdraw thresholds of control and tested compound are measured.

Example 12. Treatment of Arthritis (Prophetic Example)

Zymosan injected directly into the knee joint of mice elicits an inflammatory response and is used as a model of arthritis (Verschure et al, Ann. Rheum Dis. 53:455-460, 1994). Endpoints measured in this model include knee joint swelling score, cytokine levels in the synovial tissue and microscopic pathology of the knee.

Active compound 4-benzylsulfonyl-2-butenenitrile (50 mg/kg in vehicle) and vehicle control (1% Tween 80 in water suspension or other lipid-based pharmaceutically acceptable carrier) are administered by oral gavage to mice with a volume of 5 mL/kg.

There are 5 mice per group, with a total of 10 knees injected. On Day 1, C57BL6 mice are dosed (50 mg/kg/dose) with active compound or vehicle twice on Hours 0 and 12. On Day 2, mice are dosed with active compound or vehicle on Hour 24, then injected intra-articularly with 180 µg of zymosan (6 µL) into both knee joints on Hour 25, and then dosed a second time on Hour 36 with each active compound or vehicle. On Day 3, mice are again dosed with active compound or vehicle on Hour 48. Two hour post-dosing on Hour 50, knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-1β, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compound is expected to result in decreased inflammation as measured by a decrease in joint swelling, decrease in cytokine levels and decrease influx of inflammatory cells to the site of inflammation.

Example 13. Treatment of Gout (Prophetic Example)

Monosodium urate monohydrate (MSU) crystals injected in combination with a free fatty acid (FFA) directly into the knee joint of mice elicits an inflammatory response and is used as a model of gout (Joosten et al, Arthritis & Rheumatism, 62(11):3237-3248, 2010)). Endpoints measured in this model include knee joint swelling score, cytokine levels in the synovial tissue and microscopic pathology of the knee.

Active compound 4-benzylsulfonyl-2-butenenitrile (50 mg/kg in vehicle) and vehicle control (1% Tween 80 in water suspension or a lipid-based pharmaceutically acceptable carrier) are administered by oral gavage to mice with a volume of 5 mL/kg.

There are 5 mice per group, with a total of 10 knees injected. On Day 1, C57BL6 mice are dosed (50 mg/kg/dose) with active compounds or vehicle twice on Hours 0 and 12. On Day 2, mice are dosed with active compounds or vehicle on Hour 24, then injected intra-articularly with MSU crystals (300 µg) and C18:0 FFA (200 µM, 10 µL) on Hour 25. Three hours later (Hour 28), knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-1β, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compound is expected to result in decreased inflammation as measured by a decrease in joint swelling, decrease in cytokine levels and decrease influx of inflammatory cells to the site of inflammation.

Example 14. Treatment of Knee Pain (Prophetic Example)

Objectives:

To investigate the efficacy of the active compound in a gel formulation or in an oral formulation in patients with mild to moderate knee pain associated with osteoarthritis following temporary cessation of standard NSAID therapy. The focus of this study is on the symptoms caused by painful arthritis. The clinical trial is utilizing osteoarthritis of the knee as a well-established paradigm for other musculoskeletal disorders.

Topical Formulation:

The gel formulation containing the active compound 4-benzylsulfonyl-2-butenenitrile at 1% and 5% (Example 3) are used in this example. Placebo contains the same gel without the active compound.

Oral Formulation:

Capsules or tablets each containing 100-600 mg of the active compound 4-benzylsulfonyl-2-butenenitrile are used in this example. Placebo capsules or tablets do not contain the active compound.

Methodology:

A randomized, double-blind, placebo controlled, parallel treatment multicenter clinical activity study.

Patients with painful osteoarthritis of the knee, controlled by a stable dose of standard NSAID therapy for at least 2 months, discontinue use of the NSAIDs for a 7-day washout period. Patients are then randomized in a 1:1:1 ratio (1% active gel, 5% active gel, placebo). A total of up to 150 patients are enrolled and treated for 14 days with follow-up at 14, 21, and 28 days.

The active gel or placebo is applied to the affected knee 3 times a day for 14 days for a total of 42 treatments given every 4-6 hours while awake.

The capsules or tablets are orally administered to patients 1-4 times a day for 14 days.

Patients are treated for 14 days and followed up for a further 14 days. NSAIDs may be restarted after the Day 14 visit.

Criteria for Evaluation:

Safety:

Adverse Events throughout the study.

Physical examination at enrollment (−7 days, start of NSAID washout period), Baseline, Day 14 and Day 28.

Vital signs at enrollment (−7 days, start of NSAID washout period), Baseline and Days 7, 14, 21, 28.

Clinical laboratory measurements at Baseline, and Days 7, 14, 21 and 28.

Clinical Activity:

The primary clinical activity parameters are the measurement of pain at the site of application, as quantified by Pain on Movement assessment (100-mm VAS) and the Western Ontario and McMaster University (WOMAC) index (100-mm VAS or 5-point Likert scale). The effect of treatment on swelling, tenderness and inflammation of the knee is recorded, also the time to reduction or eradication of pain after treatment is recorded.

Study Endpoints:

The primary clinical activity endpoints are:

Change from Baseline to Day 14 in WOMAC functional disability index and sub-indices:

Pain (Scale 0-20).

Stiffness (Scale 0-8).

Physical function (Scale 0-68).

Change from Baseline (Day 1) to Day 14 in Pain on Movement (1-100 mm VAS).

The secondary clinical activity endpoints are:

Change in Current Knee Pain score (100 mm VAS) at Baseline from pre-dose to 1 hour post-dose Change in Current Knee Pain score (100 mm VAS) at Baseline from pre-dose to 2 hours post-dose Change in Global Rating of Disease (5-point Likert scale)

Time to reduction or eradication of pain subsequent to each application of active compound.

Use of rescue medication (APAP).

Proportion of subjects experiencing an improvement in Pain on Movement (100-mm VAS) from Baseline to Day 14, equal to or greater than the minimum clinically important improvement (MCII) threshold of 15 mm or 20%

Proportion of subjects whose Pain on Movement (100-mm VAS) at Day 14 is less than the Patient Acceptable Symptom State (PASS) threshold of 40 mm Proportion of subjects who are 'Responders' based on the OARSI Responder Index, in relation to WOMAC Index.

It is to be understood that the foregoing describes preferred embodiments of the present invention and that modifications may be made therein without departing from the scope of the present invention as set forth in the claims.

What is claimed is:

1. Cis-4-benzylsulfonyl-2-butenenitrile or a salt thereof.
2. Trans-4-benzylsulfonyl-2-butenenitrile or a salt thereof.
3. Cis-4-benzylsulfonyl-2-butenenitrile or a salt thereof, trans-4-benzylsulfonyl-2-butenenitrile or a salt thereof, or any combination thereof.
4. A pharmaceutical composition comprising 4-benzylsulfonyl-2-butenenitrile, or a pharmaceutically acceptable salt thereof, and a pharmaceutically acceptable carrier.
5. The pharmaceutical composition according to claim 4, wherein 4-benzylsulfonyl-2-butenenitrile is in a form of its cis-isomer, trans-isomer, or a combination of cis-isomer and trans-isomer.
6. The pharmaceutical composition according to claim 4 in a topical form of a gel, a cream, a lotion, an ointment, or a patch.
7. The pharmaceutical composition according to claim 4 in an oral form of a tablet or a capsule.
8. The pharmaceutical composition according to claim 4 in an injection form.
9. A method for treating nociceptive pain in a subject, comprising the step of administering to a subject suffering from nociceptive pain the pharmaceutical composition according to claim 4.
10. The method according to claim 9, wherein the pharmaceutical composition is administered topically.
11. The method according to claim 9, wherein the pharmaceutical composition is administered orally.
12. The method according to claim 9, wherein the pharmaceutical composition is administered by injection.
13. The method according to claim 9, wherein said nociceptive pain is caused by a skeletal or muscular disease or condition selected from the group consisting of: musculoskeletal sprains, musculoskeletal strains, tendinopathy, peripheral radiculopathy, osteoarthritis, degenerative joint disease, arthritis, gout, ankylosing spondylitis, psoriatic arthritis, systemic lupus erythematosus, costochondritis, tendonitis, bursitis, temporomandibular joint syndrome, and fibromyalgia.
14. The method according to claim 9, wherein said nociceptive pain is associated with joints, ligaments, tendons, bone, muscles, or fascia.

* * * * *